United States Patent [19]

Menhusen

[11] Patent Number: 4,696,669
[45] Date of Patent: Sep. 29, 1987

[54] HAND HELD COMBINATION FLUSH WITH ADJUSTABLE NOZZLE AND/OR SUCTION APPARATUS

[76] Inventor: Monty J. Menhusen, 2441 Winstead Cir., Wichita, Kans. 67226

[21] Appl. No.: 843,114

[22] Filed: Mar. 24, 1986

[51] Int. Cl.⁴ .............................................. A61M 1/00
[52] U.S. Cl. ...................................... 604/34; 604/35; 604/275
[58] Field of Search ....................................... 128/6–9, 128/23; 604/20–22, 27, 30, 275, 32–35, 43, 902; 417/475–477; 251/4, 6, 251

[56] References Cited

U.S. PATENT DOCUMENTS

| | | | |
|---|---|---|---|
| 811,111 | 1/1906 | Wegefarth | 604/32 |
| 1,004,369 | 9/1911 | Ciolfi | 604/21 |
| 3,191,600 | 6/1965 | Everett | 604/902 |
| 3,945,375 | 3/1976 | Banko | 128/6 |
| 4,051,867 | 10/1977 | Forborg | 251/6 |
| 4,180,074 | 12/1979 | Murry et al. | 604/119 |
| 4,204,528 | 5/1980 | Termanini | 128/6 |
| 4,270,725 | 6/1981 | Scott et al. | 251/6 |
| 4,276,023 | 6/1981 | Phillips et al. | 604/30 |
| 4,335,866 | 6/1982 | Bujan | 251/6 |
| 4,365,728 | 12/1982 | Tokorozawa et al. | 417/477 |
| 4,428,748 | 1/1984 | Peyman et al. | 604/22 |
| 4,551,130 | 11/1985 | Herbert et al. | 604/32 |
| 4,586,882 | 5/1986 | Tseng | 417/477 |
| 4,650,470 | 3/1987 | Epstein | 604/275 |

Primary Examiner—C. Fred Rosenbaum
Assistant Examiner—J. L. Kruter

[57] ABSTRACT

This invention is a hand held combination flush and/or suction apparatus including a hand held control and dispenser apparatus which can be readily held in a person's hand. The hand control and dispenser apparatus is (1) connected to a pump assembly; (2) a receiver assembly and a supply assembly operably connected to the pump assembly to provide fluid flow therethrough; and (3) an actuator assembly operable to selectively operate the pump assembly. The control and dispenser apparatus includes a main support body having an inlet and outlet assembly therethrough and a control assembly to selectively convey and monitor fluid flow therethrough. The pump assembly includes a pump roller assembly having a rotatable roller actuator members operable to engage first and second tube members to control the flow of fluid therethrough. The supply assembly operates to supply a saline fluid solution to the pump assembly. The receiver assembly is adapted to receive fluid from the pump assembly and discharge same into a vacuum receiver bottle. The actuator assembly includes a foot control assembly operable to both energize and control operation of the pump assembly and, thus, the fluid flow and vacuum through the control and dispenser apparatus.

1 Claim, 16 Drawing Figures

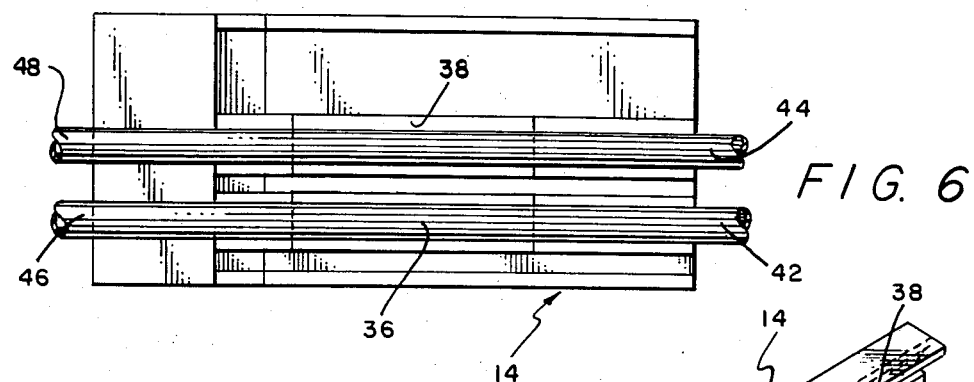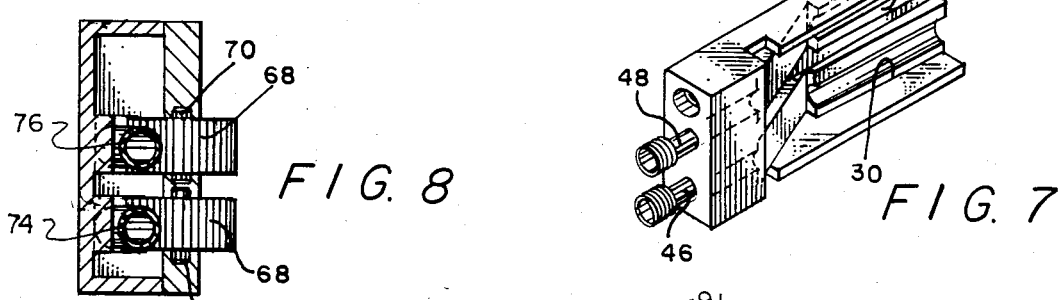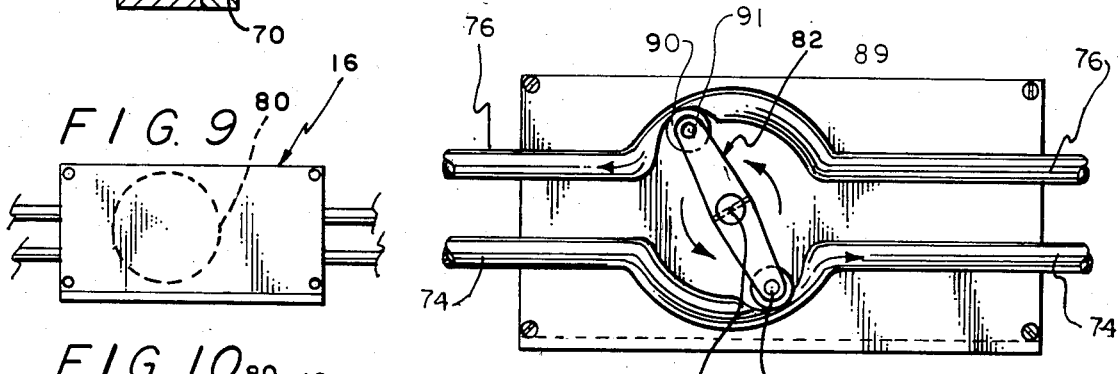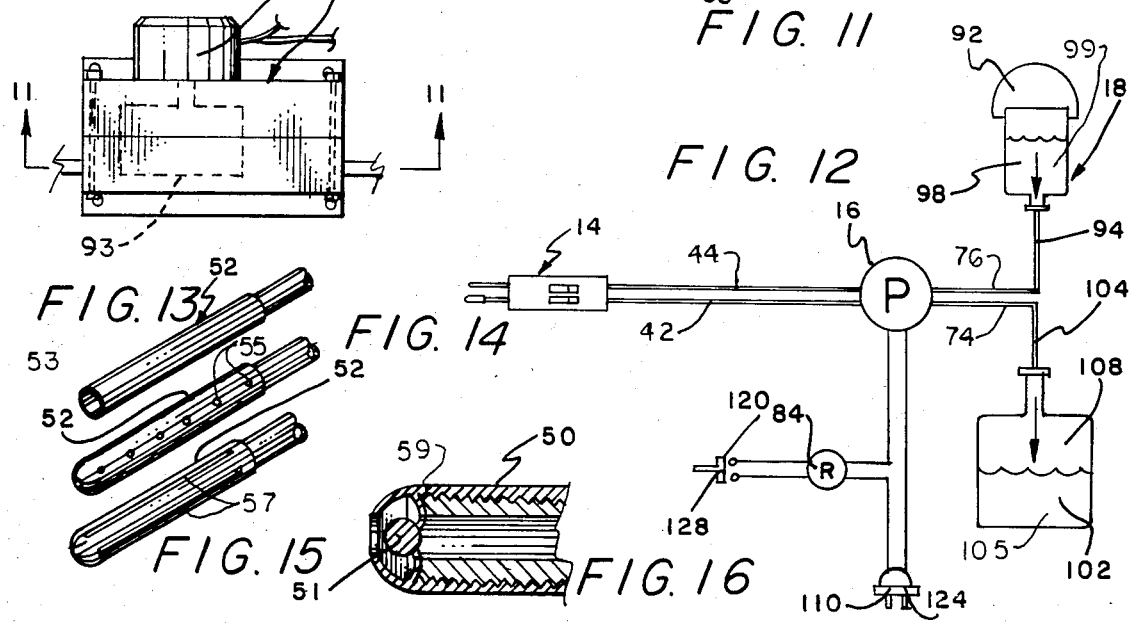

HAND HELD COMBINATION FLUSH WITH ADJUSTABLE NOZZLE AND/OR SUCTION APPARATUS

PREFERRED EMBODIMENT OF THE INVENTION

In one preferred embodiment of this invention, a hand held combination flush and/or suction apparatus normally used in medical operating procedures includes (1) a hand held control and dispenser apparatus; (2) a pump assembly connected to the hand held control and dispenser apparatus; (3) a supply assembly connected to the pump assembly to supply a fluid thereto; (4) a receiver assembly connected to the pump assembly to release fluid therefrom; and (5) an actuator assembly connected to the pump assembly to achieve selective operation thereof. The hand held control and dispenser apparatus includes a main support body having inlet and outlet assemblies connected thereto and a control assembly supported on the main support body and operably connected to the inlet and outlet assemblies to selectively control fluid flow therethrough. The outlet assembly includes outlet tube sections having (1) a spray nozzle assembly to discharge fluid therefrom; and (2) a vacuum nozzle assembly operating under a suction pressure to remove fluids from the area under medical procedure. The control assembly includes dispenser controls which are operable to selectively control the fluid flow between the inlet assembly and the outlet assembly. The pump assembly includes a pump roller assembly which, on rotation thereof, is operable to control the rate and volume of fluid flow therethrough. The pump roller assembly is connected to a rheostat member which controls power supply thereto. A supply assembly is connected by a connector tube member to the inlet assembly such as saline solution bottle. A receiver assembly is connected by a connector tube member to a vacuum receiver bottle so as to provide a fluid suction feature of this invention from the outlet assembly. The actuator assembly includes a power source connected to a foot control assembly. The foot control assembly is operable to provide the driving force to the pump assembly and selectively control operation thereof.

PRIOR ART

A search of the prior art revealed the following U.S. patents:

| Reg. No. | Patent | Inventor |
| --- | --- | --- |
| 1,686,003 | SPRAYING DEVICE | Hottinger |
| 3,016,915 | VALVE | Moeller |
| 3,099,429 | ROLLER CLAMP FOR PARENTERAL SOLUTIONS EQUIPMENT | Broman |
| 3,533,439 | ROLLER CLAMP | Hall |
| 3,802,463 | FLOW CONTROL APPARATUS | Dabney |
| 3,865,134 | SANITARY VALVE | Holcomb |

The Holcomb patent discloses a control valve system in which two (2) separate and distinct lines may be individually controlled. However, the Holcomb structure appears to be considerably complex and expensive to produce. Also, the Holcomb device requires (2) hands to operate and, thus, would not be as conveniently handled as the system set forth herein.

The Hottinger, Moller, Jr., and Hall patents each discloses systems in which two (2) flexible tubes may be throttled by application of a squeezing force from a mechanical element. However, in these systems, there is a direct relationship between increase and decrease flow in one circuit and a resultant flow in the other circuit.

The Broman and Dabney patents disclose clamp systems but they are not deemed pertinent relative to the applicant's invention herein.

Additionally, the applicant herein is aware of a device known as Simpulse Suction/Irrigator being marketed by Davol, Inc., a subsidiary of C. R. Bard, Inc. However, to the best of our knowlegde, the applicant herein is a prior inventor and, therefore, such teaching is not pertinent to the applicant's claimed invention herein.

In light of the above noted references, it is felt that the invention herein achieves numerous advantages thereover and, thus, patentable.

OBJECTS OF THE INVENTION

One object of this invention is to provide a hand held combination flush and/or suction apparatus which is selectively operated to provide (1) a saline fluid solution flushing feature when needed during medical operation procedures, and (2) a fluid suction feature directly in the area being operated on to remove undesired fluids therefrom.

One other object of this invention is to provide a hand held combination flush and/or suction apparatus which is easily held and operated in a person's single hand leaving the other hand free for other functions.

Still, one other object of this invention is to provide a hand held combination flush and/or suction apparatus which is easily grasped in one's hand having a control assembly thereon to (1) illuminate the area being operated on; and (2) easily and accurately control the amount of fluid and suction activity through dispenser controls.

One further object of this invention is to provide a hand held combination flush and/or suction apparatus including a new and novel pump assembly having a pump roller assembly controlled through a rheostat member to accurately and selectively control the amount of pumping and/or suction action obtained.

Still, another object of this invention is to provide a hand held combination flush and/or suction apparatus including a hand held control dispenser apparatus which can be selectively and closely controlled through a foot control assembly to provide a regulated amount fluid flow and suction from an area being operated upon.

One other object of this invention is to provide a hand held combination flush and/or suction apparatus which is readily held in a person's single hand; easily controlled through dispenser control knobs; sturdy in construction; reliable in operation; and substantially maintenance free.

Various other objects, advantages, and features of the invention will become apparent to those skilled in the art from the following discussion, taken in conjunction with the accompanying drawings, in which:

FIGURES OF THE INVENTION

FIG. 6 is a fragmentary sectional view taken along line 6—6 in FIG. 4;

FIG. 7 is a perspective view of a main support body of the control and dispenser apparatus;

FIG. 8 is a sectional view taken along line 8—8 in FIG. 5;

FIG. 9 is a side elevational view of the pump assembly of the combination flush and/or suction apparatus of this invention;

FIG. 10 is a top plan view of the pump assembly;

FIG. 11 is a sectional view taken along line 11—11 in FIG. 10;

FIG. 12 is a schematic diagram illustrating the operation of the combination flush and/or suction apparatus;

Figure 1:
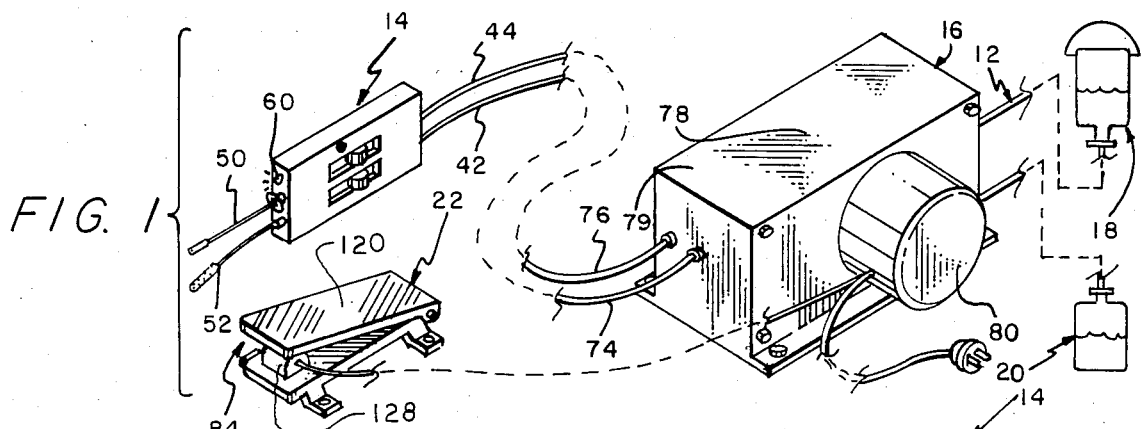
FIG. 1 is a perspective view of the hand held combination flush and/or suction apparatus of this invention.
Figure 2:
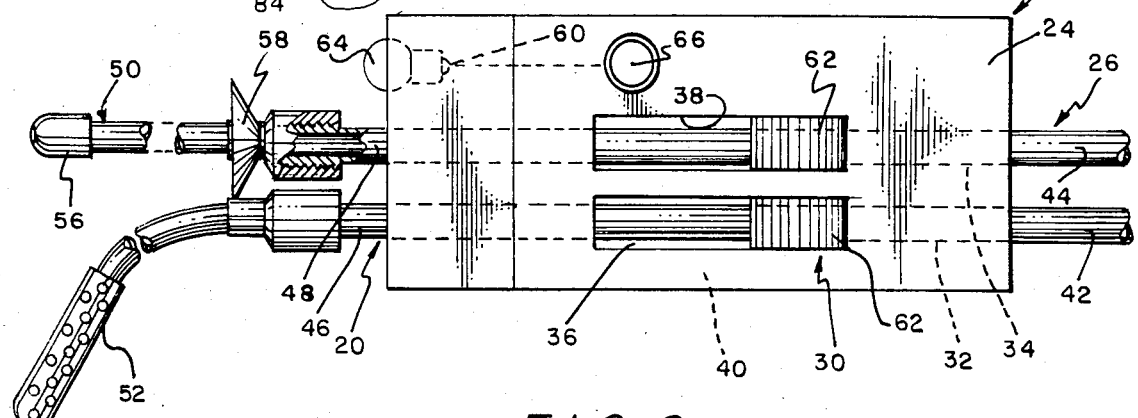
FIG. 2 is a side elevational view of a hand held control and dispenser apparatus of the combination flush and/or suction apparatus of this invention.
Figure 3:
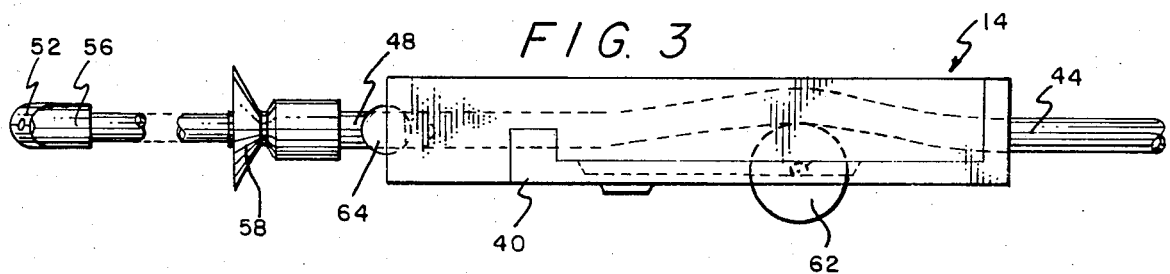
FIG. 3 is a top plan view of the control and dispenser apparatus.
Figure 4:
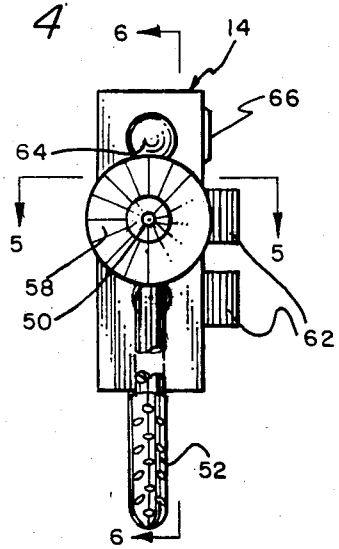
FIG. 4 is a front elevational view of the control and dispenser apparatus.
Figure 5:
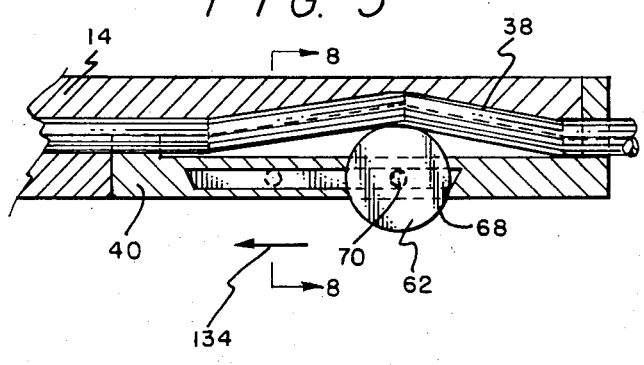
FIG. 5 is a fragmentary sectional view taken along line 5—5 in FIG. 4.

FIGS. 13, 14, and 15 are perspective views of various types of vacuum nozzle assemblies of the control and dispenser apparatus; and FIG. 16 is an enlarged fragmentary sectional view illustrating an adjustable spray nozzle assembly of the control and dispenser apparatus.

The following is a discussion and description of preferred specific embodiments of the new hand held combination flush and/or suction apparatus of this invention, such being made with reference to the drawings, whereupon the same reference numerals are used to indicate the same or similar parts and/or structure. It is to be understood that such discussion and description is not to unduly limit the scope of the invention.

DESCRIPTION OF THE INVENTION

On referring to the drawings in detail and, in particular FIG. 1, a hand held combination flush and/or suction apparatus of this invention, indicated generally at 12, is utilized as an aid for the medical profession normally during surgical operations to selectively provide a fluid flow and a fluid suction function.

More specifically, the hand held combination flush and/or suction apparatus 12 can be used on animals or humans normally during a surgical operation to provide (1) a flushing action with a saline solution to cleanse the area being operated on; and (2) a suction action to withdraw the saline solution after the cleansing function and/or blood from the area being operated upon.

The hand held combination flush and/or suction apparatus 12 includes (1) a hand held control and dispenser apparatus 14 to be grasped by one's hand; (2) a pump assembly 16 connected to the control and dispenser apparatus 14 to provide the fluid and/or suction feature; (3) a supply assembly 18 to provide the fluid supply to the pump assembly 16; (4) a receiver assembly 20 connected to the pump assembly 16 to provide a vacuum receiver; and (5) an actuator assembly 22 connected to the pump assembly 16 to control operation thereof.

The hand held control and dispenser apparatus 14 includes a main support body 24 being of a rectangular block shape having an inlet assembly 26 and an outlet assembly 28 connected thereto and a control assembly 30 operable to control fluid flow at the outlet assembly 28. The main support body 24 is provided with (1) fluid flow channels 32 and 34 therethrough; (2) actuator slots 36, 38 therein; and (3) a cover plate member 40. The fluid flow channels 32 and 34 are adapted to receive tube members therein. The actuator slots 36, 38 are adapted to receive part of the control assembly 30 and tube members therein as will be explained.

The cover plate member 40 is removably connected to the main support body 24 so as to expose a portion of the control assembly 30 and other parts for maintenance as required.

The assembly 26 includes a pair of inlet tube members 42, 44 to be placed within the respective fluid flow channels 32, 34.

The outlet assembly 28 includes outlet tube sections 46, 48 connected to the respective tube members 42, 44 and having connected thereto a vacuum nozzle assembly 52 and a spray nozzle assembly 50. The spray nozzle assembly 50 is provided with a discharge head member 56 having a conically shaped splash guard member 58 mounted thereon. The guard member 58 is operable to protect the user thereof from splash back of the fluid being dispensed therefrom.

The vacuum nozzle assembly 52 can be of various embodiments as shown in FIGS. 13, 14, and 15. As noted in FIG. 13, the vacuum nozzle assembly 52 may be of a cylindrical tubular shape with a large opening 53 at an outer end thereof. In the embodiment of FIG. 14, it is seen that vacuum nozzle assembly 52 is provided with a test tube shaped end portion 59 plurality of spaced holes 55 therein.

The embodiment of FIG. 15 is similar to FIG. 14 including the test tube shaped end portion 59 having axially extended slots 57 therein instead of a plurality of the holes 55.

As noted in FIG. 16, the spray nozzle assembly 50 may be provided with an axially movable circular seal 51 thereon whereupon an outer end portion 59 which is threaded thereon can be rotated to accurately control the fluid flow therethrough.

The control assembly 30 includes (1) a light assembly 60 mounted within the main support body 24 to illuminate the area being worked upon; and (2) a pair of dispenser controls 62. The light assembly 60 includes a light bulb member 64 activated through a light switch 66 to provide power and, thus, illumination of the light bulb member 64. The power source for the light assembly 60 may be 110 volt A.C. but preferably a battery source for safety reasons.

The dispenser control 62 includes a pair of rotatable knob members 68, each mounted on an alignment axle 70. The rotatable knob members 68 are mounted within respective ones of the actuator slots 36, 38 and being movable laterally therein to increase and decrease a clamping action on the tube members 42, 44. The actuator slots 36, 38 are inclined to vary the clamping force on the tube members 42, 44 on lateral movement. This clamping force operates to control the amount of discharge fluid flow or suction fluid flow being achieved through the hand held control and dispenser apparatus 14 of this invention. The lateral movement alignment axle 70 may be of a rack and pinion type with the actuator slots 36, 38 so that the knob members 68 remain in a given adjusted position while providing a sufficient clamping force and pressure against the respective inlet tube members 42, 44.

The pump assembly 16 includes (1) first and second tube members 74, 76 connected to the respective tube members 42, 44; (2) a main pump housing 78 being of a rectangular block shape; (3) a pump roller housing 80 connected to the main pump housing 78; (4) a pump roller assembly 82 mounted within the pump roller housing 80; and (5) a rheostat member 84 operably connected through a drive motor member to the pump roller assembly 82. The first and second tube members 74, 76 are constructed of a clear, flexible, plastic material so as to readily observe the fluid flow therethrough plus allow freedom of movement of the hand held control and dispenser aparatus 14.

The main pump housing 78 has a removable access cover 79 connected for entrance thereto to replace the tube members 74, 76 or other maintenances as required.

The pump roller assembly 82 includes a rotatable shaft member 88 connected to a linkage arm 89 having roller actuator members 90 connected to opposite ends thereof. The shaft member 88 is driven by a motor member 93 and controlled through the rheostat member 84 and the actuator assembly 22 as will be explained.

Each roller actuator member 90 is mounted on a shaft 91 and has an outer peripheral surface thereof engagable with the first and second tube members 74, 76. The rotation of the pump roller assembly 82 would determine the amount of fluid flow and/or suction to be obtained therethrough. Additionally, the shafts 91 can be adjusted towards the main shaft member 88 to regulate the amount of suction and/or fluid flow therethrough.

The rheostat member 84 is operable to achieve the desired rotational speed of the drive motor member 93 to provide an additional control function.

Ths supply assembly 18 includes (1) a fluid supply source 92; and (2) a connector tube member 94 to connect the fluid supply source 92 to the pump assembly 16. The fluid supply source 92 is normally a saline solution bottle 98 which is held in an inverted position as noted in FIG. 16 so as to supply the required fluid 99 to the pump assembly 16. Of course, various types of solution bottles 98 may be utilized as required depending on the operation being performed.

The receiver assembly 20 includes a vacuum receiver source 102 connected by a connector tube member 104 to the pump assembly 16. The vacuum receiver source 102 includes a vacuum receiver bottle 108 to receive a discharge fluid 105 therein.

The actuator assembly 22 includes a power source 110 connected to a foot control assembly 120. The power source 110 is normally a 110 volt alternating current power supply which is connected thereto through a power plug 124 in a conventional manner.

The foot control assembly 120 includes an actuator switch 128 operable through a person's foot to control speed and operation of the pump assembly 16 on driving the motor member 93 which can be additionally controlled through the rheostat member 84. The rheostat member 84 can also be controlled through depression of the foot control assembly 120.

USE AND OPERATION OF THE INVENTION

In the use and operation of the hand held combination flush and/or suction apparatus 12 of this invention, it is obvious that, initially, the pump assembly 16 is connected through the tube members 94, 104 to the respective ones of the saline solution bottle 98 and the vacuum receiver bottle 108 as noted in FIG. 16. The bottles 98, 108 are then observed during usage to assure that the solution bottle 98 does not become empty and the receiver bottle 108 does not become too full during the operation thereof.

The power source 110 is then energized through connection of the power plug 124 to a conventional electrical outlet normally of 110 A.C.

Then, the user of this invention which may normally be a doctor, would grasp the control dispenser apparatus 14 which is of such a size to be readily conveyed and held in a person's single hand. The flexible tube members 42, 44 and first and second tube members 74, 76 allow the easy movement and flexibilty of the hand held control and dispenser apparatus 14.

At this time, the control assembly 30 is operable with the light assembly 60 which can be energized through the switch 66 to illuminate the light bulb member 64. The light bulb member 64 would thereupon project a light forwardly of the hand held control and dispenser apparatus 14 directly into the area being operated upon to clearly illuminate same.

Next, the dispenser control knob members 68 may be rotatable on their respective alignement axles 70 so as to be movable laterally within the respective actuator slots 36, 38. This lateral movement of dispenser controls 62 operates with an outer surface thereof to increase and decrease the closing of the tube members 42, 44 within the actuator slots 36, 38 to respectively control the fluid flow therethrough.

On adjusting the desired fluid flow through the spray nozzle assebly 50 and the suction force being available through the vacuum nozzle assembly 52, the operator can concentrate on the area being operated upon. Also, the actuator assembly 22 through the foot control assembly 120 is operable through a person's foot to (1) control operation of the pump assembly 16 by turning the same on and off and, (2) the foot control assembly 120 is operable to control the rheostat member 84 to control operation of the motor member 89. The rheostat member 84 controls the speed of the motor member 93 so as to provide another control feature of the hand held control and dispenser apparatus 14 of this invention.

It is obvious that the cover plate member 40 can be removed from the main support body 24 of the hand held control and dispenser apparatus 14 as may be required for cleansing and maintenance.

It is noted that the splash guard member 58 about the spray nozzle assembly 50 operates as a shield to prevent spray back of the fluid being dispensed through the spray nozzle assembly 50.

As noted in FIGS. 13-15, inclusive, various types of the vacuum nozzle assemblies 52 may be utilized and illustrating three embodiments being (1) a hollow tube with an opening at an outer end thereof; (2) a cylindrical test tube type structure with a plurality of holes therein; and (3) a cylindrical test tube type structure with a plurality of elongated slots therein. These various types of vacuum nozzle assemblies 52 may be utilized depending on the animal or person being operated and the type of operation and vacuum necessary during the subject operation.

As noted in FIG. 16, the spray nozzle assembly 50 may be provided with the seal 51 whereupon the outer head portion 59 can be rotated to provide a control function for the direction and amount of fluid flow through the spray nozzle assembly 50.

The hand held combination flush and/or suction apparatus 12 of this invention can be regulated by the dispenser controls 62 and closing of the spray nozzle assembly 50 to selectively achieve only a pressure spray or vacuum function if so desired. A control valve in the connector tube members 94, 104 may be operable to close fluid flow therein to achieve the flush and/or suction function of this invention.

The hand held combination flush and/or suction apparatus of this invention can be readily held in a person's hand and controlled through a control assembly and dispenser controls to regulate the fluid flow and suction achieved therefrom. Additionally, the foot control assembly is operable to control operation of the pump assembly, and through a rheostat member, to provide another control feature of this invention. Additionally, the pump assembly includes the pump roller assemblies with the roller members 90 which can be of variable location and size to provide another control feature of this invention.

The hand held combination flush and/or suction apparatus is economical to manufacture; simple to operate; easy to maintain; and being variable and reliable in operation.

While the invention has been described in conjunction with preferred specific embodiments thereof, it will be understood that this description is intended to illustrate and not to limit the scope of the invention, which is defined by the following claims.

I claim:

1. A combination flush and/or suction apparatus operable to supply and/or remove fluid from an area being operated on, comprising:

(a) a control and dispenser apparatus which can be held in one hand of a person;

(b) a pump assembly connected to said control and dispenser apparatus to provide independently a fluid supply and a fluid suction thereto;

(c) said control and dispenser apparatus including a main support body having an inlet assembly and an outlet assembly connected thereto and having a spray nozzle assembly and a vacuum nozzle assembly projecting outwardly therefrom connected to said outlet assembly;

(d) a control assembly operably connected to the said outlet assembly to control fluid flow outwardly through said outlet spray nozzle assembly and independently control suction through said vacuum nozzle assembly; and (e) said pump assembly having first and second tube members therein and a pump roller assembly engagable with said first and second tube members; and (f) said pump roller assembly operable on rotation thereof to engage said first and second tube members to provide concurrently a fluid flow function in one of said tube members and a fluid suction function in the other tube members caused by rotation of said pump roller assembly; and said spray nozzle assembly having a chamber at its distal end thereof wherein a circular axially moveable seal means resides, said chamber being threadedly adjustable to regulate and control the flow through said distal end of the nozzle assembly.

* * * * *